(12) United States Patent
Choudhary et al.

(10) Patent No.: US 6,215,035 B1
(45) Date of Patent: Apr. 10, 2001

(54) PROCESS FOR THE PREPARATION OF ARALKYLATED AROMATIC COMPOUNDS USING HETEROGENEOUS CATALYST

(75) Inventors: Vasant Ramchandra Choudhary; Suman Kumar Jana; B-Phani Kiran, all of Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/227,825

(22) Filed: Jan. 11, 1999

(30) Foreign Application Priority Data

Sep. 25, 1998 (IN) .............................. 2877/DEL/98

(51) Int. Cl.$^7$ ..................... C07C 309/00; C07C 209/00; C07C 43/20; C07C 41/00; C07C 2/68; C07C 2/86; C07C 1/20; C07C 250/00; C07C 67/30

(52) U.S. Cl. ..................... 585/467; 585/454; 585/469; 558/369; 560/203; 562/93; 564/409; 568/628

(58) Field of Search ..................... 585/467, 454, 585/464; 558/364; 560/203; 502/93, 94; 564/404; 568/628

(56) References Cited

FOREIGN PATENT DOCUMENTS

247700 * 8/1965 (AU) .
40-17572 * 8/1965 (JP) .

* cited by examiner

*Primary Examiner*—Hien Tran
*Assistant Examiner*—Thuan D. Dang
(74) *Attorney, Agent, or Firm*—Dickinson Wright PLLC

(57) ABSTRACT

The invention relates to a process for the preparation of aralkylated aromatic compound with both small and large size aralkylating agents; wherein the catalyst used is heterogeneous solid catalyst removable from the reaction products by simple filtration, thus allowing the separated catalyst to be reused in the process. The catalyst is selected from micro or mesoporous gallosilicates and galloaluminosilicates, having structure similar to that of zeolites known in the prior art.

9 Claims, 2 Drawing Sheets $R_1R_2R_3R_4QC_nH_{2n}C_6H_3R_5R_6$ is (for Q = $C_6H_1$)

or (for Q = $C_{10}H_3$)

or (for Q = $C_{14}H_5$)

1) $R_1R_2R_3R_4QC_nH_{2n}C_6H_3R_5R_6$ is
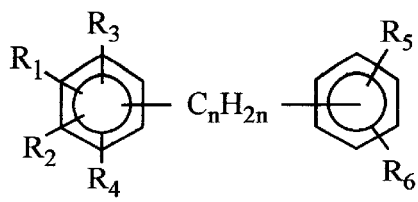 (for Q = $C_6H_1$) 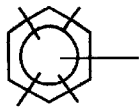
or
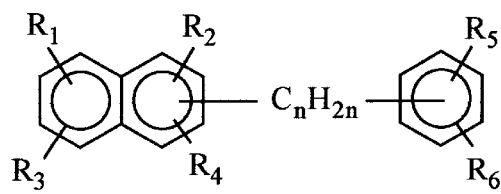 (for Q = $C_{10}H_3$) 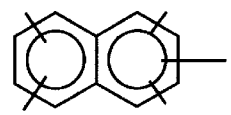
or
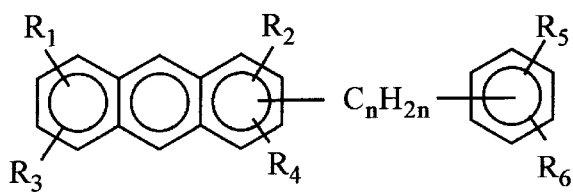 (for Q = $C_{14}H_5$) 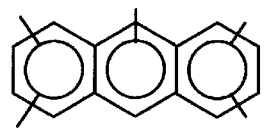
2) $R_1R_2R_3R_4M$ is
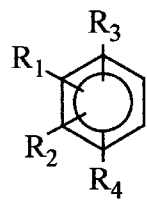 (for M = $C_6M_2$) 
or
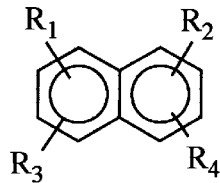 (for M = $C_{10}H_4$) 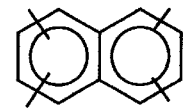

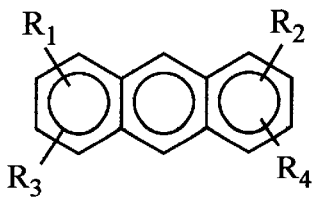
(for M = $C_{14}H_6$)
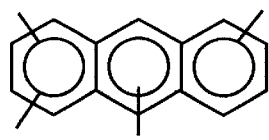
3) $XC_nH_{2n}C_6H_3R_5R_6$ is
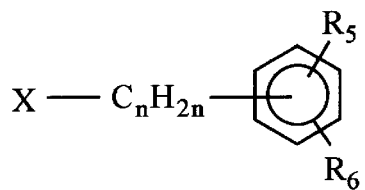   $C_6H_3$   
(where X = halogen or OH or $SO_3H$ or COOH or $OC_nH_{2n}C_6H_5$ or $OC_nH_{2n+1}$ or aryl carboxy or alkyl carboxy group).

PROCESS FOR THE PREPARATION OF ARALKYLATED AROMATIC COMPOUNDS USING HETEROGENEOUS CATALYST

This invention relates to a process for the preparation of alkylated aromatic compound by catalytic alkylation of aromatic compound with aromatic alkylating agent using a solid catalyst. This invention particularly relates to the preparation of aralkylated aromatic compound by catalytic aralkylation of aromatic compound with aromatic alkylating agent using a solid catalyst comprising of gallium.

The process for this invention could be used for the preparation of alkylated aromatic compounds, which are fine chemicals and/or used in the preparation of fine chemicals.

Aralkylated aromatic compounds are useful fine chemicals, these are also used as intermediates in a number of organic synthesis. Both the homogeneous and heterogeneous catalysed liquid phase processes for the preparation of aralkylated aromatic compounds are known in the prior art.

Homogeneous Acid Catalysed Processes

According to a U.S. patent, U.S. Pat No. 3,678,122(1972), diphenylmethane was prepared by treating a mixture of benzene and benzyl chloride with $CuCl_2$. A U.S. patent, U.S. Pat. No. 3,679,760(1972), disclosed the preparation of diaryl alkanes by refluxing benzyl chloride, $C_6H_4R_1R_2$ (where R=H and $R_2$=H, $CH_3$ or OH) and $CuCl_2$.

A French patent, Fr. Demande 2,144,578(1973), disclosed that substituted phenols p-$RC_6H_4OH$ (where R=halogen or $C_{1-4}$-alkyl) are benzylated by benzyl halides in the presence of $ZnCl_2$. A USSR patent, U.S.S.R. 394,353(1973), disclosed preparation of 2,6 and 2,4-$(CH_3O)_2$ $C_6H_3CH_2C_6H_5$ by treating m-$(CH_3O)_2$ $C_6H_4$ with benzyl chloride in the presence of $SnSO_4$ catalyst at 145–150° C., or $SnCl_2$ catalyst at 165–170° C. A Japanese patent, Japan Kokai 7399,154 (1973), disclosed preparation of dibenzyl benzene derivatives by benzylation of benzene or substituted benzenes using Friedel-Crafts catalyst e.g., $AlCl_3$, $FeCl_3$ and 98% $H_2SO_4$ According to this patent, 200 g α-methyl benzyl chloride was added to a refluxing mixture of 500 g benzene and 5 g $AlCl_3$ and the whole mixture refluxed for 5 h to give 120 g α-methyl bezylbenzene.

According to a German patent, Ger. Offen 2,456,747 (1976), o-benzyltoluenes were prepared in ~90% yields by the reaction of α o-chloromethyltoluene with a benzene derivative in ≧1:7 ratio in the presence of $H_2SO_4$ and/or $H_3PO_4$ and optionally 4-$CH_3C_6H_4SO_3H$, $ZnCl_2$, $BF_3$, etc. Thus 135 parts 85% $H_3PO_4$, 270 parts 85% $H_2SO_4$, 10 parts 4-$CH_3C_6H_4SO_3H$, 70 parts $2CH_3C_6H_4CH_2Cl$ and 390 parts of $C_6H_6$ were heated at 75–80° C. for 4 h to give 89% 2-$CH_3C_6H_4CH_2C_6H_5$.

An US Patent U.S. Pat. No. 4,049,733 (1977), disclosed preparation of diphenylmethane by benzylation of benzene with benzylether using phosphoric acid and optionally $H_2SO_4$ or a Friedel-Crafts type metal halide.

European patent, Eup.Pat.Appl.EP 37,628 (1981), disclosed preparation of diphenylmethane by benzylation of benzene with chloromethylbenzenes in the presence of $H_2SO_4$ and a cationic surfactant or a non-ionic surfactant which is susceptible to protonation under strong acidic conditions.

A German patent, Ger.Offen DE 3,922,518 (1991), disclosed a process for the manufacture of α-methylbenzylphenol derivatives, which comprises the treatment of $C_{1-4}$-alkyl substituted phenols with styrene in the presence of phosphorus chloride catalyst. More recently, an European Patent, Eur.Pat.Appl.EP 538,704 (1993), disclosed a process for the preparation of p-substituted o-benzylphenols by treating phenols, p-$R'C_6H_4OH$ (R'= halo, alkyl, OH, alkoxy, ikylmercapto, aryl, aryloxy. or arylmercapto), with $ArCH_2X$ (Ar=corresponding aryl nucleus; X=halo, arylcarboxy, phenylsulfatoxy, hydroxy, alkoxy etc.) in a continuously functioning distillation apparatus in the presence of dissolved acid catalyst.

The main disadvantages of the homogeneous acid catalyzed processes are as follows:

1) The separation and recovery of the dissolved acid catalysts from the liquid reaction mixture is difficult.
2) The disposal of the used acid catalysts creates environmental pollution.
3) The homogeneous acid catalysts also pose several other problems such as high toxicity, corrosion, spent acid disposal and use of more than the stoichiometric amount.

Heterogeneous Acid Catalyzed Processes

A German patent, Ger.Offen 2,547,030 (1977), disclosed the preparation of o-benzyltoluenes by the reaction of o-methylbenzyl halides with substituted benzenes in the presence of Al-silicate. The 2-$CH_3C_6H_4CH_2Cl$ was stirred with toluene and Al-silicate (25% $Al_2O_3$) at 110° C. to give 81% 2-methylbenzyltoluene. According to a Japanese patent, Jpn. Kokai Tokkyo Koho JP 59,186,937 (1984), o-benzylphenol was prepared by the liquid phase reaction of benzyl alcohol with phenol in the presence of λ-$Al_2O_3$. For exanple 7.5 g γ-$Al_2O_3$ was added to a mixture of 32.5 g benzyl alcohol and 47 g phenol at 190° C. under stirring to give a product containing 49.9% o-benzylphenol. A German Patent, Ger. Offen DE 3,700,917 (1988), disclosed the preparation of p-substituted o-benzylphenols by benzylation of p-substituted phenols with benzylalcohol in the presence of Na-Y type zeolite. A mixture of 0.5 mole 4-$ClC_6H_4OH$, 0.1 mole $C_6H_5CH_2OH$ and 0.6 g of Na-Y type zeolite was heated at 200° C. for 3 hrs to give 25.4% 2-benzyl-4-chlorophenol.

A German patent, Ger. Offen DE 3,836,780 (1990), disclosed thesprocess for the preparation of benzylbenzenes from benzenes and benzyl alcohols in the presence of activated bleaching earth and a diluent at 90–140° C. According to Japanese patent, Jpn Kokai Tokkyo Koho JP 03,170,442 (1991), benzylbiphenyls are manufactured by benzylating biphenyl and diphenylmethane with ≧1 compound from benzyl halides, benzyl alcohol, benzyl ether in the presence of a zeolite or silica-alumina catalyst. An European patent, Eur.Pat. appl. EP 428,081 (1991), disclosed a process of benzylation of alkylbenzenes with benzyl chloride in the presence of H—Y or H—L zeolite catalyst. According to a Gerrnan patent, Ger. Offen DE 4,038,933 (1992), disclosed a process for benzylation of aromatics using technical carbon catalysts.

Aralkylation of aromatic compounds by aralkylating agent involves electrophilic substitution of H from the aromatic nucleus. It is well known, in the prior art that the electrophilic substitution is favoured by the presence of electron donating groups, such as OH, alkyl, alkoxy, phenoxy, amine, alkyl amine, SH etc., in the aromatic compound to be aralkylated. Whereas the electrophilic substitution is inhibited by the presence of electron withdrawing groups such as halo, nitro, cyano, carboxy, aldehyde, etc., in the aromatic compound to be aralkylated. [ref. G. A. Olah, in Friedel-Crafts and related reactions, Wiley-Interscience Publ., New York, 1963].

Although some limitations of the homogeneous acid catalyzed processes are overcome by the prior art heterogeneous catalyzed processes described above, the aralkylating activity of the solid catalysts used in the prior art processes are low, particularly for aralkylating aromatic compounds containing electron withdrawing groups. Hence there is a great practical need for finding more efficient solid catalyst for the aralkylating of aromatic compounds. There is also a need for finding highly efficient solid catalyst also for the aralkylating of aromatic compounds containing electron withdrawing groups such as halo, nitro, cyano, carboxy, aldehyde, etc. This invention is, therefore, made with the following objects so that most of the drawbacks or limitations of the prior art homogeneous and heterogeneous catalyzed processes for the preparation of aralkylated aromatic compounds could be overcome.

OBJECTS OF THE INVENTION

1. Accordingly, the main object of this invention is to provide a liquid phase process for the preparation of aralkylated aromatic compound by aralkylating aromatic compound with aralkylating agent, using a highly active solid catalyst comprising of gallium, which has high activity not only when the aromatic ring activating groups (i.e. electron donating groups) are present in the aromatic ring to be aralkylated but also when aromatic ring deactivating groups (i.e. electron withdrawing groups) are present in the aromatic ring to be aralkylated, so that the reaction temperature is low and/or time for completing the reaction is short.
2. Another important object of this invention is to provide a liquid phase process for the preparation of aralkylated aromatic compound by aralkylating aromatic compound with aralkylating agent, using highly active solid catalyst comprising of gallium, which can be reused repeatedly for the catalytic reaction.

This invention provides a process for the preparation of aralkylated aromatic compound, represented by a general chemical formula: $R_1R_2R_3R4QC_nH_{2n}C_6H_3R_5R_6$, having structural formula (1) of the drawing accompanying the specification by the arallkylation of aromatic compound, represented by a general chemical formula: $R_1R_2R_3R_4M$, having structural formula (2) of the drawing accompanying the specification with aralkylating agent, represented by a general chemical formula: $R_5R_6C_6H_3C_nM_{2n}X$, having structural formula (3) of the drawing accompanying the specification wherein Q is $C_6H_1$ or $C_{10}H_3$ or $C_{14}H_5$; M is $C_6H_2$ or $C_{10}H_4$ or $C_{14}H_6$; each of $R_1$, $R_2$, $R_3$ and $R_4$ groups is H or $C_nH_{2n+1}$ or $C_pH_{2p-1}$ or $C_6H_5$ or $C_nH_{2n}C_6H_5$ or OH or $OC_nH_{2+1}$ or $OC_6H_5$ or halogen or $C_nH_{2n+1-x}Y_x$ or $NO_2$ or $NH_2$ or $NHC_nH_{2n+1}$ or $N(C_nH_{2n+1})_2$ or $NHCOC_nH_{2n+1}$ or $NHCOC_6H_5$ or CN or CHO or COOH or $COOC_nH_{2n+1}$ or $COC_nH_{2n+1}$ or $SO_3H$ or $SO_3C_nH_{2n+1}$ or SH or alkyl mercapto group or aryl mercapto group; each of $R_5$ and $R_6$ group is H or $CH_3$ or $C_2H_5$ or OH or $OCH_3$ or $OC_2H_5$ or $NO_2$ or halogen or $NH_2$; X is halogen or OH or $SO_3H$ or COOH or $OC_nH_{2n}C_6H_5$ or $OC_nH_{2+1}$ or aryl carboxy group or alkyl carboxy group, x is an integer between 1 and 2n+1 n & p are integers greater than or equal to 1 and 2, respectively, and C,H,N,O and S are chemical elements, using a solid catalyst comprising gallium. which comprises:

i) pretreating said solid catalyst at a temperature between about 100° C. and about 800° C. in a flow of moisture-free air or inert gas at a gas hourly space velocity in the range 1000–20000 $cm^3g^{-1}h^{-1}$ or under vacuum, for a period between about 0.1 h and about 10 h.

ii) contacting a liquid mixture of said aromatic compound and said aromatic aralkylating agent having a mole ratio of said aromatic compound to the said aromatic aralkylating agent between about 0.5 and about 50, in the absence or presence of a suitable solvent selected from nitrobenzene, nitromethane and liquid paraffinic hydrocarbons, with a mole ratio of said solvent to said aralkylating agent between about 0 and about 50 with said pretreated solid catalyst at a weight ratio of solid catalyst to said aromatic aralkylating agent between about 0.02 and about 2.0 in a stirred batch reactor fitted with a reflux condenser, under vigorous stirring, while bubbling continuously a moisture-free inert gas, such as helium, nitrogen or argon, through the said liquid reaction mixture containing the said catalyst at a flow rate above 0.1 $cm^3$ of inert gas per $cm^3$ of liquid reaction mixture per minute and allowing the reaction to occur at a temperature between about 25° C. and about 300° C. at a pressure between about 1 atm and about 10 atm for a reaction period between about 0.01 h and about 50 h, and iii) cooling the reaction mixture to a temperature about 25° C., removing said catalyst from the reaction mixture by filtration and then separating the reaction products from the reaction mixture by the methods known in the prior art.

SUMMARY OF THE INVENTION

The main finding of this invention is that, the said catalyst shows high activity in the aralkylation of aromatic compounds not only when the electron donating group, which is aromatic ring activating group, is present in the aromatic ring to be aralkylated but also when the electron withdrawing group, which is aromatic ring deactivating group, is present in the aromatic ring to be aralkylated, so that the reaction temperature is low and/or the time required for completing the reaction is short.

Other important finding of this invention is that said solid catalyst can be reused repeatedly in the aralkylation of said aromatic compounds. Yet another important finding of this invention is that the mechanism of the aralkylation of aromatic compounds over said solid catalyst is different from that of acid-catalyzed Friedel-Crafts aralkylation reaction.

BRIEF DESCRIPTION OF THE DRAWING

The FIGURE shows general chemical formula of reactants and product of the process.

DETAILED DESCRIPTION OF THE INVENTION

Accordingly this invention provides a process for the preparation of aralkylated aromatic compound represented by a general chemical formula: $R_1R_2R_3R_4QC_nH_{2n}C_6H_3R_5R_6$, having structural formula (1) of the drawing accompanying the specification by the aralkylation of aromatic compound, represented by a general chemical formula: $R_1R_2R_3R_4M$, having structural formula (2) of the drawing accompanying the specification with aralkylaiting agent, represented by a general chemical formula: $R_5R_6C_6H_3C_nH_{2n}X$, having structural fornula (3) of the drawing accompanying the specification Wherein Q is $C_6H_1$ or $C_{10}H_3$ or $C_{14}H_5$; M is $C_6H_2$ or $C_{10}H_4$ or $C_{14}H_6$; each of $R_1$, $R_2$,$R_3$ and $R_4$ groups is H or $C_nH_{2n+1}$ or $C_pH_{2p-1}$ or $C_nH_{2n+1}$ or $C_nH_{2n}C_6H_5$ or OH or $OC_nH_{2n+1}$ or $OC_6H_5$ or halogen or $C_nH_{2n+1-x}Y_x$ or $NO_2$ or $NHC_nH_{2n+1}$ or $N(C_nH_{2n+1})_2$ or $NHCOC_nH_{2n+1}$ or $NHCOC_6H_5$ or CN or CHO or COOH or $COOCC_nH_{2n+1}$ or $COC_nH_{2n+1}$ or $SO_3H$ or $SO_3Cs_nH_{2n+1}$ or SH or $SC_nH_{2n+1}$ or alkyl mercapto group or aryl mercapto group; each of $R_5$ and $R_6$ group is H or $CH_3$ or $C_2H_5$ or OH or $OCH_3$ or $OC_2H_5$ or $NO_2$ or halogen or $NH_2$; X is halogen or OH or $SO_3H$ or COOH or $OC_nH_{2n}C_6H_5$ or $OC_nH_{2n+1}$ or aryl carboxy group or alkyl carboxy group, x is an integer between 1 and 2n+1 and n & p are integers greater than or equal to 1 and 2, respectively, and C,H,N,O and S are chemical elements, using a solid catalyst comprising gallium, which comprises:

i) pretreating solid catalyst at a temperature between about 100° C. and 800° C. in a flow of moisture-free air or inert gas at a gas hourly space velocity in the range 1000–20000 $cm^3g^{-1}h^{-1}$ or under vacuum, for a period between about 0.1 h and about 10 h.

ii) contacting a liquid mixture of said aromatic compound and said aromatic aralkylating agent having a mole ratio of said aromatic compound to the said aromatic aralkylating agent between 0.5 and about 50, in absence or presence of a suitable solvent selected from nitrobenzene, nitromethane and liquid paraffinic hydrocarbons with a mole ratio of said solvent to said alkylating agent between 0 and 50 with said pretreated solid catalyst at a weight ratio of solid catalyst to said aromatic alkylatin agent between about 0.02 and 2.0 in a stirred batch reactor fitted with a reflux condenser, under vigorous stirring, while continuously bubbling a moisture-free inert gas, such as helium, nitrogen or argon, through the said reaction mixture containing the said catalyst at a flow rate above 0.1 $cm^3$ inert gas per $cm^3$ of liquid reaction mixture per minute and allowing the reaction to occur at a temperature between about 25° C. and about 300° C. at a pressure of about 1 atm and about 10 atm for a reaction period between about 0.01 h and about 50 h.

iii) cooling the reaction mixture to a temperature about 25° C., removing the said catalyst from the reaction mixture by filtration and then separating the reaction products from the reaction mixture by methods known in the prior art.

In the process of the present invention, the preferred reaction temperature is between about 50° C. and about 200° C.; the preferred reaction pressure is between about 1 atm and about 5 atm; the preferred reaction period is between about 0.05 h and about 20 h; the preferred mole ratio of said aromatic compound to said aralkylating agent is between about 1and about 20; the preferred weight ratio of said catalyst to said aralkylating agent is between about 0.05 and about 0.5.

In the process of the present invention, a preferred said catalyst is selected from micro or mesoporous gallosilicates and galloaluminosilicates, having structure similar to that of zeolites known in the prior art; $Ga^{+3}$-exchanged micro and mesoporous zeolites and cationic clays; micro or mesoporous gallophosphates or galloaluminophosphates; $Ga_2O_3$ and/or Ga-halide impregnated or deposited on micro and mesoporous zeolites, crystalline micro and mesoporous alumino- and metallo-phosphates, cationic and anionic clays, microporous and mesoporous metal oxides or mixed metal oxides and macroporous catalyst supports; gallium oxide pillared clays; and gallium oxide.

A more preferred said catalyst for the process of this invention is selected from H-gallo- and H-galloaluminosilicates of ZSM-5 and MCM-41 type zeolites; $Ga_2O_3$ or $Ga_2O_3$ deposited on H-ZSM-5 zeolite, MCM-41 zeolite macroporous catalyst supports comprising of silica, alumina, silicon carbide or $ZrO_2$ and $HfO_2$ or their mixture; and $GaCl_3$ impregnated on Montmorillonite K10 clay or high silica MCM-41.

The process of this invention can be carried out in a stirred batch reactor, fitted with a reflux condenser and arrangement for bubbling inert gas through the reaction mixture, known in the prior art for carrying out liquid phase reactions.

In the process of this invention, the main products formed are said aralkylated aromatic compound and a by-product HX, wherein H=hydrogen and X=halogen or OH or $SO_3H$ or COOH or $OC_nH_{2n}C_6H_5$ or $OC_nH_{2n+1}$ or arylcarboxy group or alkylcarboxy group, depending upon said aralkylating agent used.

In the process of this invention, said aromatic compound and said aralkylating agent are reactants and are converted partially or completely to said products.

In the process of this invention, the role of said solvent, if used, is to dissolve solid reactant or reactants, to dilute reactants acd/or to facilitate the reaction between said aromatic compound and said aralkylating agent. However, solvent may not be used in the process of this invention when both the reactants are liquid at said reaction conditions. Nomially, said solvent is not converted in the process of this invention.

In the process of this invention, the role of inert gas bubbling continuously through the reaction mixture is to remove continuously said by-product from the reaction-mixture so that the reverse reaction is avoided or minimised and the time required for completing the reaction is shortened.

In the process of this invention, the role of th e reflux condenser fitted with the reactor is to condense reactants and solvents and to return them back to the reaction mixture and allow the inert gas, which is continuously bubbling through the reaction mixture, along with said by-product to escape from the reaction mixture.

In the process of this invention, the reaction pressure above atmospheric pressure may be used to allow the reaction to be carried out at temperature higher than the normal boiling point of the reactants and/or solvent, by increasing, the boiling point of said reactants and/or solvent with increasing the reaction pressure.

Said catalyst, used in the process of this invention, is heterogeneous with respect to the reaction mixture and can be removed from the reaction mixture simply by filtration and the removed catalyst, after washing with solvent or said liquid aromatic compound which is to be aralkylated, can be reused in the said process.

Said pretreatment to said catalyst in step-i of the process of present invention is necessary for removing moisture adsorbed on the catalyst so that the catalyst shows its full efficiency for catalysing the reaction between said aromatic compound and said aralkylating agent.

The role of gallium compound present in said catalyst is to activate both the reactants, said aromatic compound and said aralkylating agent. The $R_5R_6C_6H_3C_nH_{2n}\ldots X$ bond of said aralkylating agent is weakened by its interaction with said gallium compound, leading to the formation of a stable carbocation $[R_5R_6C_6H_3C_nH_{2n}]^+$ (I) and $X^-$. In the presence of said carbocation (X), said aromatic compound is activated on gallium compound by weakening its bond between aromatic nucleus and H, leading to the formation of a penta-coordinated carbocation by the combination of said activated aromatic corpound and said carbocation (I). The said penta-coordinated carbocation is then decomposed to said aralkylated aromatic compound, the main product of the reaction, and a proton, which combines with $X^-$ to give HX, the by-product of the reaction.

Said catalyst used in the process of invention can be prepared by various methods, such as hydrothermal synthesis, impregnation, coating, cation exchange, coprecipitation and pillaring of clays, all known in the prior art.

Zeolites are crystalline aluminosilicates containing well defined chanjnels or pores of uniform diameter. A large number of microporous zeolites, such as X, Y, mordenite, L, beta, ZSM-5, ZSM-8, ZSM-11, etc., and mesoporous zeolites, such as M41S type material, e.g. MCM-41, are known in the prior-art. [ref. Breck in Zeolite Molecular Sieves, Wiley-Interscience Publ., New York, 1974; Beck and Co-workers. J.Am.Chem.Soc., vol.114, page 10834, year 1992; Nature (London) vol.359, page 710, year 1992].

In general, micropores have diameter below 1 nm; mesopores have diameter between about 1 nm and about 20 nm; and macropores have diameter above about 20 nm. Said catalyst containing only micropores may be used in the process of this invention when both the reactants have minimum molecular diameter or critical size less than 0.7 nm. Whereas said catalyst containing meso and/or macropores may be used in the process of this invention for both small and large molecular size reactants.

By the process of this invention, benzene, nitrobenzene (which contains highly deactivating electron withdrawing group $NO_2$) and anthracene can be benzylated with benzyl chloride to corresponding aralkylated aromatic compound with a benzyl chloride conversion of 95%, 95% and 95%, respectively, at 1 atm pressure, temperature 80° C., 135° C. and; ,130° C., respectively and reaction period 0.16 h, 0.27 h and 0.31 h, respectively, using $Ga_2O_3$ (10 wt %) supported on commercial low surface area (<1 m²) macroporous silica-alumina catalyst carrier.

The present invention is described with respect to the following examples illustrating the process. of this invention for the preparation of aralkylated aromatic compounds. These examples are provided for illustrative purposes only and are not to be construed as limitations on the process of this invention.

Definition of Terms Used in the Examples

Conversion of reactant (%)=mole % of the reactant converted to all products. All the ratios of said aromatic compounds to said aralkylating agent and of said solvent to said aralkylatying agent are mole ratios. The said catalyst to the said aralkylating agent ratio is weight ratio.

The flow rates of gases are measured at 0° C. and 1 atm pressure. Gas hourly space velocity (GHSV) is volume of gas, measured at 0° C. and 1 atm pressure, passed over unit mass of catalyst per hour.

Ac and Aa represent aromatic compound to be aralkylated and aralkylating agent, respectively.

The micropores, mesopores and macropores have pore diameter of below 1.0 nm, between about 1.0 nm and about 20 nm, and above about 20 nm, respectively.

EXAMPLE-1

This example illustrates the process of this invention for the benzylation of benzene, nitrobenzene, m-xylene, p-xylene, durene (1,2,4,5 tetramethylbenzene) napthalene and anthracene by benzyl chloride or benzyl bromide to the corresponding benzylated aromatic compounds, using $Ga_2O_3$ supported on a commercial macroporous silica alumina (SA 5205) catalyst carrier as a catalyst.

The supported $Ga_2O_3$ catalyst, $Ga_2O_3$ (10 wt. %)/SA 5205, was prepared by depositing the required amount of gallium nitrate from its aqueous solution on the commercial support SA 5205 ( obtained from M/s. NORTON Co. U.S.A.), having main chemical composition: 11.8% $SiO_2$, 86.1% $Al_2O_3$; surface area<0.01 $m^2g^{-1}$, pore volume 0.35 $cm^3g^{-1}$ and average pore diameter ~200 mm and particle size 100–150 mesh, by incipient wetness technique, drying the impregnated mass at 120° C. for 6 h and calcining at 450° C. for 4 h.

The catalytic benzylation reaction over the $Ga_2O_3$/SA 5205 was carried out by i) pretreating the catalyst in a quartz tubular reactor under a flow of moisture-free helium at a gas hourly space velocity of 18,000 cm 3 $g^{-1}$ $h^{-1}$ at 400° C. for 1 h and then ii) contacting said pretreated catalyst with 15 cm³ liquid reaction mixture containing aromatic, compound to be benzylated and the benzylating agent and optionally a solvent, in a stirred batch reactor (capacity 50 cm³) fitted with a reflux condenser, mercury thermometer dipped in the reaction mixture and an inlet tube for passing gas through the reaction mixture, under vigorous stirring, while bubbling moisture-free $N_2$ gas through the reaction mixture at the reaction conditions given in TABLES-1 and 2 and following the course of the reaction by measuring quantitatively the HCl or HBr evolved during the reaction by absorbing it in aqueous NaOH solution by a simple acid-base titration using phenolphthalein indicator, and iii) cooling the reaction mixture to room temperature (25° C.) and analysing the products and unconverted reactants present in the reaction mixture, after separating the solid catalyst from it by filtration, using chromatographic technique.

The results are: included in TABLES-1 and 2.

TABLE 1

Reaction conditions and results of the aralkylation of different aromatic compounds over $Ga_2O_3$(10 wt. %)/SA 5205 catalyst.

| Reactants: | | | | |
|---|---|---|---|---|
| Aromatic compound (Ac) | $C_6H_6$ (benzene) | $C_{10}H_8$ (napthalene) | $C_{14}H_{10}$ (anthracene) | $(CH_3)_4C_6H_2$ (durene) |
| Aralkylating agent (Aa) | $C_6H_5CH_2Cl$ | $C_6H_5CH_2Cl$ | $C_6H_5CH_2Cl$ | $C_6H_5CH_2Cl$ |
| Reaction Conditions: | | | | |
| Solvent | nil | n-octane | n-octane | n-octane |
| Ac/Aa mole ratio | 16.8 | 1.4 | 1.1 | 1.3 |
| Solvent/Aa mole ratio | 0.0 | 9.4 | 12.4 | 9.4 |

TABLE 1-continued

Reaction conditions and results of the aralkylation of different aromatic compounds over $Ga_2O_3$(10 wt. %)/SA 5205 catalyst.

| Catalyst/Aa weight ratio | 0.1 | 0.1 | 0.1 | 0.1 |
|---|---|---|---|---|
| Temperature (° C.) | 80.0 | 82.0 | 130.0 | 110.0 |
| Pressure (atm) | 1.0 | 1.0 | 1.0 | 1.0 |
| $N_2$ flow ($cm^3min^{-1}$) | 30.0 | 30.0 | 2S.0 | 30.0 |
| Reaction time (h) | 0.20 | 0.33 | 0.31 | 0.45 |
| Conversion of aralkylating agent (%) | 95.0 | 95.0 | 95.0 | 95.0 |
| Main product of reaction | $C_6H_5CH_2C_6H_5$ (diphenyl-methane) | $C_{10}H_7CH_2C_6H_5$ (benzyl napthalene) | $C_{14}H_9CH_2C_6H_5$ (benzyl anthracene) | $(CH_3)_4C_6H_1CH_2C_6H_5$ (benzyl durene) |
| By-product of reaction | HCl | HCl | HCl | HCl |

Ac = Aromatic compound, Aa = Aralkylating agent

TABLE 2

Reaction conditions and results of the aralkylation of different aromatic compounds over $Ga_2O_3$(10 wt. %)/SA 5205 catalyst.

| Reactants: | | | | |
|---|---|---|---|---|
| Aromatic compound (Ac) | $C_6H_5NO_2$ (nitrobenzene) | $C_6H_5NO_2$ (nitrobenzene) | m-$C_6H_4$- (m-xylene) | p-$C_6H_4$- (p-xylene) |
| Aralkylating agent (Aa) | $C_6H_5CH_2Cl$ | $C_6H_5CH_2Cl$ | $C_6H_5CH_2Br$ | $C_6H_5CH_2Br$ |
| Reaction Conditions: | | | | |
| Solvent | nil | n-heptane | nil | nil |
| Ac/Aa mole ratio | 14.63 | 1.13 | 12.55 | 12.55 |
| Solvent/Aa mle ratio | 0.0 | 10.22 | 0.0 | 0.0 |
| Catalyst/Aa weight ratio | 0.1 | 0.1 | 0.1 | 0.1 |
| Temperature (° C.) | 135.0 | 135.0 | 130.0 | 130.0 |
| Pressure (atm) | 1.0 | 4.9 | 1.0 | 1.0 |
| $N_2$ flow ($cm^3min.^{-1}$) | 30.0 | 30.0 | 50.0 | 50.0 |
| Reaction time (h) | 0.27 | 0.27 | 0.25 | 0.50 |
| Conversion of aralkylating agent (%) | 95 | >99 | 95 | >99 |
| Main product of reaction | $NO_2C_6H_4CH_2C_6H_5$ (benzyl nitrobenzene) | $NO_2C_6H_4CH_2C_6H_5$ (benzyl nitrobenzene) | $(CH_3)_2C_6H_3CH_2C_6H_5$ (benzyl m-xylene) | $(CH_3)_2C_6H_3CH_2CH_5$ (benzyl p-xylene) |
| By-product of reaction | HCl | HCl | HBr | HBr |

Ac = Aromatic compound, Aa = Aralkylating agent

EXAMPLE-2

This example illustrates the process of this invention for the benzylation of benzene and different substituted benzenes by benzyl chloride or benzyl alcohol, as an aralkylating agent, to corresponding benzylated aromatic compounds, using ZSM-5 type microporous H-galloalumino silicate, as a catalyst, in powder form.

The ZSM-5 type H-galloalumino silicate, having Ga/Al= 3, Si/(Al+Ga)=11.7, and degree of $H^+$exchange>98% and crystal size=4–6 μm, was prepared by the procedure known in the prior art [ref Choudhary et al., Journal of Catalysis, vol. 158, page 23 and year 1996; Zeolites vol. 18, page 274 and year 1997].

The catalytic benzylation of benzene and substituted benzenes by benzyl chloride or benzyl alcohol over the H-galloalumino silicate catalyst was carried out by the procedure samne as that described in EXAMPLE-1 at the reaction conditions given in TABLES-3 and 4. The results are included in TABLES-3 and 4.

TABLE 3

Reaction conditions and results of the aralkylation of different aromatic compounds over a solid catalyst, H-galloalumino silicate of ZSM-5 type.

Reactants:

| | | | | |
|---|---|---|---|---|
| Aromatic compound (Ac) | $C_6H_6$ (benzene) | $CH_3C_6H_5$ (toluene) | $CH_3C_6H_5$ (toluene) | $C_6H_5Cl$ (Chlorobenzene) |
| Aralkylating agent (Aa) | $C_6H_5CH_2Cl$ | $C_6H_5CH_2Cl$ | $C_6H_5CH_2OH$ | $C_6H_5CH_2Cl$ |

Reaction Conditions:

| | | | | |
|---|---|---|---|---|
| Solvent | nil | nil | nil | nil |
| Ac/Aa mole ratio | 16.85 | 14.03 | 12.61 | 14.61 |
| Solvent/Aa mole ratio | 0.0 | 0.0 | 0.0 | 0.0 |
| Catalyst/Aa weight ratio | 0.1 | 0.1 | 0.1 | 0.1 |
| Temperature (° C.) | 80.0 | 80.0 | 110.0 | 80.0 |
| Pressure (atm) | 1.0 | 1.0 | 1.0 | 1.0 |
| $N_2$ flow ($cm^3 min^{-1}$) | 30.0 | 30.0 | 30.0 | 40.0 |
| Reaction time (h) | 1.1 | 0.33 | 15.0 | 0.60 |
| Conversion of aralkylating agent (%) | 95 | 95 | >99.9 | 95 |
| Main product of reaction | $C_6H_5CH_2C_6H_5$ (diphenyl-methane) | $CH_3C_6H_4CH_2C_6H_5$ (benzyltoluene) | $CH_3C_6H_4CH_2C_6H_5$ (benzyltoluene) | $ClC_6H_4CH_2C_6H_5$ (benzyl chlorobenzene) |
| By-product of reaction | HCl | HCl | HCl | HCl |

Ac = Aromatic compound, Aa = Aralkylating agent

TABLE 4

Reaction conditions and results of the aralkylation of different aromatic compounds over a solid catalyst, H-galloalumino silicate of ZSM-5 type.

Reactants:

| | | | | |
|---|---|---|---|---|
| Aromatic compound (Ac) | $CH_3OC_6H_5$ (anisole) | $C_5H_5OH$ (phenol) | $C_6H_6$ (benzene) | $C_6H_6$ (benzene) |
| Aralkylating agent (Aa) | $C_6H_5CH_2Cl$ | $C_6H_5CH_2Cl$ | $C_6H_5CH_2CH_2Cl$ | $CH_3C_6H_4CH_2Cl$ |

Reaction Conditions:

| | | | | |
|---|---|---|---|---|
| Solvent | nil | n-octane | nil | nil |
| Ac/Aa mole ratio | 13.81 | 1.01 | 19.27 | 19.27 |
| Solvent/Aa mole ratio | 0.0 | 9.45 | 0.0 | 0.0 |
| Catalyst/Aa weight ratio | 0.1 | 0.1 | 0.1 | 0.1 |
| Temperature (° C.) | 80.0 | 80.0 | 80.0 | 80.0 |
| Pressure (atm) | 1.0 | 1.0 | 1.0 | 1.0 |
| $N_2$ flow ($cm^3 min^{-1}$) | 40.0 | 40.0 | 30.0 | 30.0 |
| Reaction time (h) | 1.0 | 1.33 | 4.0 | 6.0 |
| Conversion of aralkylating agent (%) | 95 | 95 | >99 | >99 |
| Main product of reaction | $CH_3OC_6H_4CH_2C_6H_5$ (benzyl anisole) | $HOC_6H_4CH_2C_6H_5$ (benzyl phenol) | $C_6H_5CH_2CH_2C_6H_5$ | $C_6H_5CH_2C_6H_4CH_3$ |
| By-product of reaction | HCl | HCl | HCl | HCl |

Ac = Aromatic compound
Aa = Aralkylating agent

EXAMPLE-3

This example illustrates the process of this invention for the preparation of benzyl benzene and benzyl toluene by benzylation of benzene and toluene, respectively, with benzyl chloride in the absence of any solvent, over H-gallosilicate of ZSM-5 type, as a catalyst, in the form of powder.

The H-gallosilicate (ZSM-5 type), having Si/Ga=33 and degree of H+exchange>95% and crystal or particle size=5–6 μm, was prepared by the procedure described earlier [ref. Choudhaty et al., Journal of Catalysis, volume 158, page 34 and year 1996].

The catalytic benzylation of benzene and toluene by benzyl chloride over H-gallosilicate catalyst was carried out by the procedure same as that described in EXAMPLE-1 at the reaction conditions given in TABLE-5, except that the catalyst pre-treatment was caried out under vacuum (2 torr pressure) at 600° C. for 0.5 h. The results are included in TABLE-5.

H+exchange>99.0% and crystal size 3–5 μm), silica gel (Fuji Davison, A-type, surface area 720 $m^2g^{-1}$), γ-$Al_2O_3$ (surface area 155 $m^2g^{-1}$) and high silica MCM-41 [prepared by the procedure described in the ref. Choudhary et al., Proceeding of Indian Academy of Sciences, (Chemical Sciences) volume 109, page 229 and year 1997], respectively, in powder form, by incipient wetness technique, drying the impregnated mass at 120° C. for 10 h and calcining at 500° C. for 6 h.

The catalytic aralkylation of benzene by different aralkylating agents over each of the above catalysts was carried out by the procedure same as that described in EXAMPLE-1 at

TABLE 5

Reaction conditions and results of the aralkylation of benzene and toluene over H-gallosilicate of ZSM-5 type, as a catalyst.

Reactants:

| | | | | |
|---|---|---|---|---|
| Aromatic compound (Ac) | $C_6H_6$ (benzene) | $CH_3C_6H_5$ (toluene) | $C_6H_6$ (benzene) | $CH_3C_6H_5$ (toluene) |
| Aralkylating agent (Aa) | $C_6H_5CH_2Cl$ | $C_6H_5CH_2Cl$ | $C_6H_5CH_2Cl$ | $C_6H_5CH_2Cl$ |
| Reaction Conditions: | | | | |
| Solvent | nil | nil | nil | nil |
| Ac/Aa mole ratio | 16.85 | 14.03 | 16.85 | 14.03 |
| Solvent/Aa mole ratio | 0.0 | 0.0 | 0.0 | 0.0 |
| Catalyst/Aa weight ratio | 0.1 | 0.1 | 0.1 | 0.1 |
| Temperature (° C.) | 80.0 | 80.0 | 80.0 | 80.0 |
| Pressure (atm) | 1.0 | 1.0 | 1.0 | 1.0 |
| $N_2$ flow ($cm^3min^{-1}$) | 30.0 | 30.0 | 30.0 | 30.0 |
| Reaction time (h) | 0.35 | 0.15 | 1.2 | 1.0 |
| Conversion of aralkylating agent (%) | 50 | 50 | 90 | >99 |
| Main product of reaction | $C_6H_5CH_2C_6H_5$ (benzylbenzene) | $CH_3C_6H_4CH_2C_6H_5$ (benzyltoluene) | $C_6H_5CH_2C_6H_5$ (benzylbenzene) | $CH_3C_6H_4CH_2C_6H_5$ (benzyltoluene) |
| By-product of reaction | HCl | HCl | HCl | HCl |

Ac = Aromatic compound, Aa = Aralkylating agent

EXAMPLE-4

This example illustrates the process of this invention for the preparation of aralkylated benzene by the aralkylation of benzene with different aralkylating agents, using $Ga_2O_3$ (obtained from M/s Aldrich Chemicals, U.S.A.) and $Ga_2O_3$ supported on microporous H-ZSM-5 and silica gel, micro and mesoporous γ-$Al_2O_3$ and mesoporous high silica MCM41, as catalysts, in the absence of any solvent.

The $Ga_2O_3$ (3.0 wt. %)/H-ZSM-5, $Ga_2O_3$ (10 wt. %)/$SiO_2$ gel, $Ga_2O3$ (10 wt. %)/γ-$Al_2O_3$ and $Ga_2O_3$ (10 wt.)/highsilica MCM-41 catalysts were prepared by depositing the required amount of gallium nitrate from its aqueous solution on H-ZSM-5 (Si/Al=35.0, degree of the reaction conditions given in TABLE-6, except that in the present case the pretreatment of the catalyst was carried out in the flow of moisture-free $N_2$ at 500° C. at a gas hourly space velocity of 3000 $cm^3.g^{-1}.h^{-1}$ for 2 h. The results are included in TABLE-6.

The results in TABLE-6 show that the $Ga_2O_3$ and supported $Ga_2O_3$ catalysts except $Ga_2O_3$/γ-$Al_2O_3$, show high activity in the benzylation of benzene. However, it may be noted that the support alone, i.e. H-ZSM-5 zeolite, silica gel, γ-alumina and high silica MCM41 zeolite, showed no activity in the benzylation of benzene at the said reaction conditions.

TABLE 6

Reaction conditions and results of the aralkylation of benzene over $Ga_2O_3$ supported on different catalyst carriers, as a catalyst.

| Catalyst | 3.0 wt % $Ga_2O_3$/ H ZSM-S | 10 wt % $Ga_2O_3$/ $SiO_2$ gel | 10 wt % $Ga_2O_3$/ γ-$Al_2O_3$ | 10 wt % $Ga_2O_3$/ MCM-41 | $Ga_2O_3$ |
|---|---|---|---|---|---|

TABLE 6-continued

Reaction conditions and results of the aralkylation of benzene over $Ga_2O_3$ supported on different catalyst carriers, as a catalyst.

| Reactants: | | | | | |
|---|---|---|---|---|---|
| Aromatic compound (Ac) | $C_6H_6$ (benzene) | $C_6H_6$ (benzene) | $C_6H_6$ (benzene) | $C_6H_6$ (benzene) | $C_6H_6$ (benzene) |
| Aralkylating agent (Aa) | $C_6H_5CH_2Cl$ | $C_6H_5CH_2Cl$ | $C_6H_5CH_2Cl$ | $C_6H_5CH_2Cl$ | $C_6H_5CH_2Cl$ |
| Reaction Conditions: | | | | | |
| Solvent | nil | nil | nil | nil | nil |
| Ac/Aa mole ratio | 16.85 | 16.85 | 16.85 | 16.85 | 16.85 |
| Solvent/Aa mole ratio | 0.0 | 0.0 | 0.0 | 0.0 | 0.0 |
| Catalyst/Aa weight ratio | 0.1 | 0.1 | 0.1 | 0.1 | 0.1 |
| Temperature (° C.) | 80.0 | 80.0 | 80.0 | 80.0 | 80.0 |
| Pressure (atm) | 1.0 | 1.0 | 1.0 | 1.0 | 1.0 |
| $N_2$ flow ($cm^3 min^{-1}$) | 30.0 | 30.0 | 30.0 | 30.0 | 30.0 |
| Reaction time (h) | 0.5 | 0.5 | 0.5 | 0.5 | 0.16 |
| Conversion of of aralkylating agent (%) | >99 | 90 | 15 | 100 | 100 |
| Main product of reaction | $C_6H_5CH_2C_6H_5$ (diphenylmethane) | $C_6H_5CH_2C_6H_5$ (diphenylmethane) | $C_6H_5CH_2C_6H_5$ (diphenylmethane) | $C_6H_5CH_2C_6H_5$ (diphenylmethane) | $C_6H_5CH_2C_6H_5$ (diphenylmethane) |
| By-product of reaction | HCl | HCl | HCl | HCl | HCl |

Ac = Aromatic compound, Aa = Aralkylating agent

EXAMPLE-5

This example illustrates the process of this invention for the benzylation of benzene and substituted benzenes by benzyl chloride to corresponding benzylated aromatic compounds, using $GaCl_3$ impregnated Montmorillonite K10 clay catalyst in the absence of a solvent.

The $GaCl_3$ (10 wt. %)/Montmorillonite KIO clay catalyst was prepared by impregnating required amount of $GaCl_3$ from its dry acetonitrile solution on Montmorillonite K10 clay (obtained from Aldrich Chemicals co. U.S.A.) in powder form, following the incipient wetness technique and drying the impregnated mass at 60° C. under vacuum for 10 h.

The catalytic benzylation of benzene and substituted benzenes by benzyl chloride over the above catalyst has been carried out by the procedure same as that described in EXAMPLE-1, at the reaction conditions given in TABLE-7, except that in the present case the pretreatment of the catalyst was carried out at 120° C. in the flow of moisture-free helium gas at a gas hourly space velocity of 6000 $cm^3 g^{-1} h^{-1}$ for 5 h. The results are included in TABLE-7.

TABLE 7

Reaction conditions and results of the aralkylation of different aromatic compounds over $GaCl_3$/Montmorillonite K10, as a catalyst.

| Reactants: | | | | |
|---|---|---|---|---|
| Aromatic compound (Ac) | $C_6H_6$ (benzene) | $CH_3C_6H_5$ (toluene) | $NO_2C_6H_5$ (nitrobenzene) | $CH_3C_6H_5$ (toluene) |
| Aralkylating agent (Aa) | $C_6H_5CH_2Cl$ | $C_6H_5CH_2Cl$ | $C_6H_5CH_2Cl$ | $C_6H_5CH_2Cl$ |
| Reaction Conditions: | | | | |
| Solvent | nil | nil | nil | nil |
| Ac/Aa mole ratio | 16.85 | 14.03 | 14.63 | 14.03 |
| Solvent/Aa mole ratio | 0.0 | 0.0 | 0.0 | 0.0 |
| Catalyst/Aa weight ratio | 0.1 | 0.1 | 0.1 | 0.1 |
| Temperature (° C.) | 80.0 | 80.0 | 80.0 | 80.0 |
| Pressure (atm) | 1.0 | 1.0 | 1.0 | 1.0 |
| $N_2$ flow ($cm^3 min^{-1}$) | 30.0 | 40.0 | 40.0 | 40.0 |

TABLE 7-continued

Reaction conditions and results of the aralkylation of different aromatic compounds over GaCl$_3$/Montmorillonite K10, as a catalyst.

| | | | | |
|---|---|---|---|---|
| Reaction time (h) | 0.3 | 0.25 | 0.20 | 1.0 |
| Conversion of aralkylating agent (%) | 95 | 95 | 95 | >99 |
| Main product of reaction | C$_6$H$_5$CH$_2$C$_6$H$_5$ (diphenylmethane) | CH$_3$C$_6$H$_4$CH$_2$C$_6$H$_5$ (benzyltoluene) | NO$_2$C$_6$H$_4$CH$_2$C$_6$H$_5$ (benzyl nitrobenzene) | CH$_3$C$_6$H$_4$CH$_2$C$_6$H$_5$ (benzyltoluene) |
| By-product of reaction | HCl | HCl | HCl | HCl |

Ac = Aromatic compound, Aa = Aralkylating agent

EXAMPLE-6

This example illustrates the process of this invention for the benzylation of toluene by benzyl chloride using Ga$_2$O$_3$/SA 5205 catalyst prepared in EXAMPLE-1, and reused of this catalyst for the subsequent reactions carried out in a number of batches. The benzylation reactions was carried out using the Ga$_2$O$_3$/SA 5205 catalyst, prepared in EXAMPLE-1, and by the procedure same as that described in EXAMPLE-1, at the reaction conditions given in TABLE-8, except that in the present case the catalyst used in the second and onward batches was not given said pretreatment, Instead the catalyst obtained by filtration from the reaction mixture of first batch was used as it is, after washing it with toluene, for the second batch reaction, and so on. The results are given in TABLE-8. The results show that the catalyst can be reused repeatedly for the process.

The main advantages of the process of this invention over the prior art processes for the preparation of aralkylated aromatic compounds are as follows:

1) The process of this invention has a number of advantages over the earlier homogeneous catalysed processes for the preparation of aralkylated aromatic compounds, as follows:
   In the process of this invention
   i) the catalyst used is heterogeneous solid catalyst and hence it can be separated from the reaction products simply by filtration,
   ii) the separated catalysts can be reused in the process for a number of times, and
   iii) also the catalyst is non corrosive, therefore most of the serious problems associated with homogeneous catalyst used in the earlier homogeneous catalysed processes for the preparation of aralkylated aromatic compounds are overcome in the process of this invention.

TABLE 8

Reaction conditions and results of the aralkylation of toluene by benzyl chloride over Ga$_2$O$_3$(10 wt %)/SA 5205 catalyst, fresh and reused in the subsequent batches.

| Batch | 1 | 2 | 3 | 4 |
|---|---|---|---|---|
| Catalyst | Fresh Ga$_2$O$_3$/SA 5205(after pretreated as described in EXAMPLE-1) | that used in batch 1, after separating it by filtration and washing with toluene | that used in batch 2, after separating it by filtration and washing with toluene | that used in batch 3, after separating it by filtration and washing with toluene |
| Reaction Conditions: | | | | |
| Solvent | nil | nil | nil | nil |
| Ac/Aa mole ratio | 14.03 | 14.03 | 14.03 | 14.03 |
| Solvent/Aa mole ratio | 0.0 | 0.0 | 0.0 | 0.0 |
| Catalyst/Aa weight ratio | 0.1 | 0.1 | 0.1 | 0.1 |
| Temperature (° C.) | 80.0 | 80.0 | 80.0 | 80.0 |
| Pressure (atma) | 1.0 | 1.0 | 1.0 | 1.0 |
| N$_2$ flow (cm$^3$min$^{-1}$) | 40.0 | 40.0 | 40.0 | 40.0 |
| Reaction time (h) | 0.16 | 0.075 | 0.5 | 0.5 |
| Conversion of aralkylating agent (%) | 95 | 70 | >99 | >99 |
| Main product of reaction | CH$_3$C$_6$H$_4$CH$_2$C$_6$H$_5$ (benzyltoluene) | CH$_3$C$_6$H$_4$CH$_2$C$_6$H$_5$ (benzyltoluene) | CH$_3$C$_6$H$_4$CH$_2$C$_6$H$_5$ (benzyltoluene) | CH$_3$C$_6$H$_4$CH$_2$C$_6$H$_5$ (benzyltoluene) |
| By-product of reaction | HCl | HCl | HCl | HCl |

Ac = Aromatic compound, Aa = Aralkylating agent

2) The process of this invention has also number of advantages over the prior art processes based on the use of solid catalyst for the preparation of aralkylated aromatic compounds, as follows:
  i) The activity of the said catalyst used in the process of present invention is higher.
  ii) The process of the present invention can be used for aralkyating both small and large size aromatic compounds with both small and large size aralkylating agents to produce the corresponding aralkylated compounds.
  iii) In the process of this invention, since moisture-free inert gas is bubbled through the reaction mixture continuously, said by-product formed in the reaction is removed continuously and thereby the reverse aralkylation reaction is avoided or minimised, thus requiring shorter time for completing the reaction,
  iv) In the process of this invention, it is possible to carry out the aralkylation reaction at a temperature higher than the normal boiling point of either of the reactants and the solvent, and thereby the reaction period for completing the reaction is shortened and/or the inhibition of the reaction due to strong adsorption of the reactants, products or solvent on the catalyst is avoided or minimised,
  v) By the process of this invention, the aralkylation of said aromatic compound is possible at mild reaction conditions even though when the aromatic compound does not contain any aromatic nucleus activating group or electron donating group, for example when aromatic compound is benzene, or when said aromatic compound contains electron withdrawing group, for example halide or nitro group, which has highly deactivating effect on the aromatic nucleus for the aralkylation reaction.

We claim:

1. A process for the preparation of aralkylated aromatic compound, represented by a general chemical formula: $R_1R_2R_3R_4QC_nH_{2n}.C_6H_3R_5R_6$ having structural formula

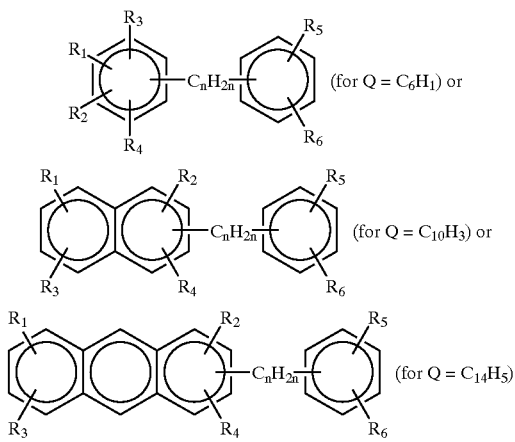

by the aralkylation of aromatic compound, represented by a general chemical formula: $R_1R_2R_3R_4M$, having structural formula

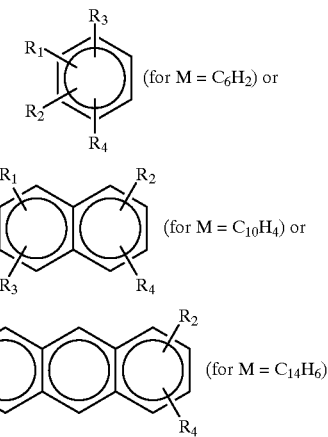

with aralkylating agent, represented by a general chemical formula: $R_5R_6C_6H_3C_nH_{2n}X$, having structural formula

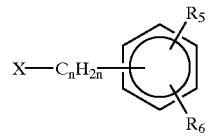

wherein Q is $C_6H_1$ or $C_{10}H_3$ or $C_{14}H_5$; M is $C_6H_2$ or $C_{10}H_4$ or $C_{14}H_6$; each of $R_1$, $R_2$ $R_3$ and $R_4$ groups is H or $C_nH_{2n+1}$ or $C_pH_{2p-1}$ or $C_6H_5$ or $C_nH_{2n}C_6H_5$ or OH or $OC_nH_{2n+1}$ or $OC_6H_5$ or halogen or $NO_2$ or $NH_2$ or $NHC_nH_{2n+1}$ or $N(C_nH_{2n+1})_2$ or $NHCOC_nH_{2n+1}$ or $NHCOC_6H_5$ or CN or CHO or COOH or $COOC_nH_{2n+1}$ or $COC_nH_{2n+1}$ or $SO_3H$ or $SO_3C_nH_{2n+1}$ or SH or alkyl mercapto group or aryl mercapto group; each of $R_5$ and $R_6$ group is H or $CH_3$ or $C_2H_5$ or OH or $OCH_3$ or $OC_2H_5$ or $NO_2$ or halogen or $NH_2$; X is halogen or OH or $SO_3H$ or COOH or $OC_nH_{2n}C_6H_5$ or $OC_nH_{2n+1}$ or aryl carboxy group or alkyl carboxy group, x is an integer between 1 and 2n+1 and n and p are integers greater than or equal to 1 and 2, respectively, and C,H,N,O and S are chemical elements, using a solid catalyst comprising gallium, which comprises:
  i) pretreating said solid catalyst at a temperature between about 100° C. and about 800° C. in a flow of moisture-free air or inert gas at a gas hourly space velocity in the range 1000–20000 $cm^3g^{-1}h^{-1}$ or under vacuum, for a period between about 0.1 h and about 10 h,
  ii) contacting a liquid mixture of said aromatic compound and said aromatic aralkylating agent having a mole ratio of said aromatic compound to the said aromatic aralkylating agent between about 0.5 and about 50, in the absence or presence of a solvent, wherein the solvent is a material selected from the group consisting of nitrobenzene, nitromethane and liquid paraffinic hydrocarbons, with a mole ratio of said solvent to said alkylating agent between about 0 and about 50 with said pretreated solid catalyst at a weight ratio of solid catalyst to said aromatic alkylating agent between about 0.02 and about 2.0 in a stirred batch reactor fitted with a reflux condenser, under vigorous stirring, while bubbling continuously a moisture-free inert gas through the said liquid reaction mixture containing the said catalyst at a flow rate above 0.1 $cm^3$ of inert gas per $cm^3$ of liquid reaction mixture per minute and allowing the reaction to occur at a temperature between about 25° C. and about 300° C. at a pressure between about 1 atm and about 10 atm for a reaction period between about 0.01 h and about 50 h, and iii) cooling the reaction mixture to a temperature about 25° C., removing said catalyst from the reaction mixture by filtration and then separating the reaction products from the reaction mixture.

2. A process as claimed in claim 1, wherein the reaction temperature is between 50° C. and 200° C.

3. A process as claimed in claim 1, wherein the reaction pressure is between about 1.0 atm to about 5.0 atm.

4. A process as claimed in claim 1, wherein the reaction period is between about 0.05 h and about 20 h.

5. A process as claimed in claim 1, wherein the mole ratio of said aromatic compound to said aralkylating agent is between about 1 and about 20.

6. A process as claimed in claim 1, wherein a weight ratio of said catalyst to said aralkylating agent is between about 0.05 to about 0.5.

7. A process as claimed in claim 1, wherein said catalyst is (1) micro or mesoporous gallosilicates or galloalumino-silicates having structure similar to that of zeolites; (2) $Ga^{+3}$-exchanged micro or mesoporous zeolites or cationic clays; (3) micro or mesoporous gallophosphates or galloaluminophosphates; (4) $Ga_2O_3$ and/or Ga-halide impregnated or deposited on micro or mesoporous zeolites, crystalline micro or mesoporolfs alumino-, silico-alumino or metallophosphates, cationic or anionic clays, microporous or mesoporous metal oxides or mixed metal oxides, or macroporous catalyst supports; (5) gallium oxide pillared clays; or (6) gallium oxide.

8. A process as claimed in claim 1, wherein said catalyst is (1) H-gallo- and H-galloalumino-silicates of ZSM-5 and MCM41 zeolites; $Ga_2O_3$ or $Ga_2O_3$ deposited on H-ZSM-5 zeolite, MCM-41 zeolite or macroporous catalyst supports are silica, alumina, silicon carbide, $ZrO_2$ and $HfO_2$ or their mixture; or (3) $GaCl_3$ impregnated on Montmorillonite K10 clay or high silica MCM41.

9. A process as claimed in claim 7, wherein said catalyst is (5) H-gallo- and H-galloalumino-silicates of ZSM-5 and MCM41 zeolites; (2) $Ga_2O_3$ or $Ga_2O3$ deposited on H-ZSM-5 zeolite, MCM41 zeolite or macroporous catalyst supports are silica, alumina, silicon carbide or, $ZrO_2$ and $HfO_2$ or their mixture; and (3) GaCl3 impregnated on Montmorillonite K10 clay or high silica MCM-41.

* * * * *